United States Patent [19]
Ribi

[11] Patent Number: 4,844,894
[45] Date of Patent: Jul. 4, 1989

[54] METHOD OF INHIBITING THE ONSET OF SEPTICEMIA AND ENDOTOXEMIA

[75] Inventor: Edgar E. Ribi, deceased, late of Hamilton Mont. by Karin S. Ribi, administratrix

[73] Assignee: Ribi Immunochem Research Inc., Hamilton, Mont.

[21] Appl. No.: 934,627

[22] Filed: Nov. 25, 1986

Related U.S. Application Data

[63] Continuation-in-part of Ser. No. 630,013, Jul. 12, 1984, Pat. No. 4,629,722.

[51] Int. Cl.$^4$ ............................................. A61K 37/20
[52] U.S. Cl. ..................................... 424/88; 424/92; 514/23; 514/54; 514/917; 514/921
[58] Field of Search .................... 424/88, 92; 514/23, 514/54, 917, 921

[56] References Cited

U.S. PATENT DOCUMENTS

| 3,438,865 | 4/1969 | Work et al. | 424/92 |
| 4,029,762 | 6/1977 | Galands et al. | 424/92 |
| 4,436,728 | 3/1984 | Ribi et al. | 530/407 |
| 4,663,306 | 5/1987 | Cantrell | 435/68 |

FOREIGN PATENT DOCUMENTS 0174204  3/1986  European Pat. Off. ............ 435/240

OTHER PUBLICATIONS

Ziegler et al., *Jama* vol. 307(20) 1982, pg. 1225.
Hinshaw et al., *CA* vol. 87, #9 56n; 1977.
Balogh et al. *CA* vol. 97, 1982 #86685q.
Balogh et al. *CA* vol. 101, 1984 #103796X.
Tomai et al., *CA* vol. 107, 1987 #17442w.
Masihi et al., *CA* vol. 105, 1986, #95672u.
Ribi et al., *CA* vol. 105, 1986 #53908v.
Chase et al., *Inf. and Immunity* 53(3) 1986, pp. 711–712.
"Infection and Immunity", Aug. 1984, p. 350–355 (esp. 352).

*Primary Examiner*—Howard E. Schain
*Assistant Examiner*—Garnette D. Draper

[57] ABSTRACT

The present invention is directed to a method of inhibiting to onset of septicemia and endotoxemia. The methods comprise administering to a warm-blooded animal an effective amount of a pharmaceutical composition comprising Monophosphoryl lipid A in combination with a pharmaceutically acceptable carrier.

13 Claims, No Drawings

METHOD OF INHIBITING THE ONSET OF SEPTICEMIA AND ENDOTOXEMIA

This application is a continuation-in-part of application Ser. No. 630,013, filed July 12, 1984 now U.S. Pat. No. 4,629,722 the entire contents of which are incorporated herein by reference.

FIELD OF THE INVENTION

The present invention is directed to a method of inhibiting the onset of septicemia in warm-blooded animals. In another aspect, the present invention is also directed to a method of inhibiting the onset of septic and non-septic endotoxemia. Each of the methods comprises administering to a warm-blooded animal an effective amount of a pharmaceutical composition comprising refined detoxified endotoxin (RDE), hereinafter also referred to as Monophosphoryl Lipid A (MPL), in combination with a pharmaceutically acceptable carrier.

BACKGROUND OF THE INVENTION

Septicemia is a clinical syndrome in which infection is disseminated through the body by the blood stream. It is a potentially disastrous blood infection that can be caused by a variety of microorganism. It is a pathological state which results from the presence of microorganisms and/or their poisonous by-products in the blood stream. One particularly common form of septicemia, involving infection by gram-negative bacteria, is referred to as gram-negative bacteremia.

A survey in 1974 reported that septicemia strikes 71,000 people in the United States annually, resulting in death in approximately 25% of the cases. One of the major causes of septicemia is post-operative infection resulting from endogenous bacteria from the respiratory or gastrointestinal tract (See Cruse, P. J. E., et al. Arch., Surg. 107, 106–210, 1973, incorporated herein by reference).

Endotoxemia is a condition caused by the presence of endotoxins in the blood and is commonly associated with severe hypotension that is usually fatal. Shock induced by injecting laboratory animals with endotoxin produces pathophysiologic changes similar to that of gram-negative bacteremic shock in humans. More recently, evidence has suggested that shock syndrome in man is associated with endotoxemia. As in the case of septicemia, endotoxemia affects large numbers of people annually, and is fatal in 60% or more of the cases (see for example RJ Hamill and DG Maki. Endotoxin shock in man caused by gram-negative bacilli. In RA Proctor (Ed), *Clinical Aspects of Endotoxin Shock*, Vol 4, pp 55–126: 1986. Elsevier, Amsterdam—N.Y.).

In the New England Journal of Medicine, Volume 307, No. 20, Nov. 11, 1982, an article was published by Elizabeth J. Ziegler et al. on the treatment of gram-negative bacteremia and shock with human antiserum to a mutant *Escherichia coli*. It was disclosed in this reference that septicemia can be treated by injection of anti-endotoxin serum. Hence, the reference does not disclose the use of endotoxin or its derivatives per se, but discloses the use of antibodies directed against endotoxins. This approach was also discussed in an article in Medical World News, June 24, 1985, and a paper by Teng et al., Proc. Nat. Acad. Sci. 82, 1790:1985, wherein it was indicated that monoclonal antibodies (mAbs) against endotoxin are used instead of anti-endotoxin sera. While the antiserum is a highly heterogeneous substance, the mAbs are pure proteins of known structure. Moreover, in these references, the antiserum and the mAbs are used to treat patients suffering from gram-negative septicemia, i.e., they are used therapeutically and not prophylactically.

In an article by A. Balogh et al., Chem. Abstracts, No. 86685(q) Vol. 97, 1982 entitled "Effect of Pretreatment with Radiation—Detoxified Endotoxin on the Endotoxin Shock of Dogs", it was reported that a radiation-detoxified endotoxin preparation identified as "Tolerin" prevented the drop in blood pressure and decrease of cardiac output that appears in the acute phase of endotoxin shock. The endotoxin shock had been induced by administration of *Escherichia coli* endotoxin.

In another article by A. Balogh, Chem. Abstracts No. 103796x Vol 101, 1982, entitled "Prevention of the Irreversiblity of Surgical Shocks with Radiation Detoxified Endotoxin Pretreatment" it was also reported that gamma-irradiation - detoxified *Escherichia coli* endotoxin prevented the lethal effects of septic shock in rats and dogs.

Thus, prior to the present invention, the use of Monophosphoryl Lipid A, had not been disclosed in the literature as being useful in preventing septicemia or endotoxemia.

It is therefore an object of the invention to provide a method of inhibiting the onset of septicemia in warm-blooded animals using a therapeutic composition containing Monophosphoryl Lipid A.

It is another aspect of the invention to provide a method of inhibiting the onset of endotoxemia in warm-blooded animals using a therapeutic composition containing Monophosphoryl Lipid A.

SUMMARY OF THE INVENTION

The present invention is directed to a method of inhibiting the onset of septicemia in a warm-blooded animal which comprises administering to the warm-blooded animal, an effective amount of a composition comprising Monophosphoryl Lipid A and a pharmaceutically acceptable carrier. The present invention is also directed to a method of inhibiting the onset of endotoxemia in warm-blooded animals comprising administering to warm-blooded animals, an effective amount of a composition comprising Monophosphoryl Lipid A and a pharmaceutically acceptable carrier.

Monophosphoryl Lipid A (MPL), is a composition characterized as having no detectable 2-keto-3-deoxyoctanoate, between about 350 and 475 nmoles/mg of phosphorus and between about 1700 and 2000 nmoles/mg of fatty acids. The complete structure of a Monophosphoryl lipid A obtained from lipopolysaccharides of *Salmonella minnesota* R595 has been given as follows.

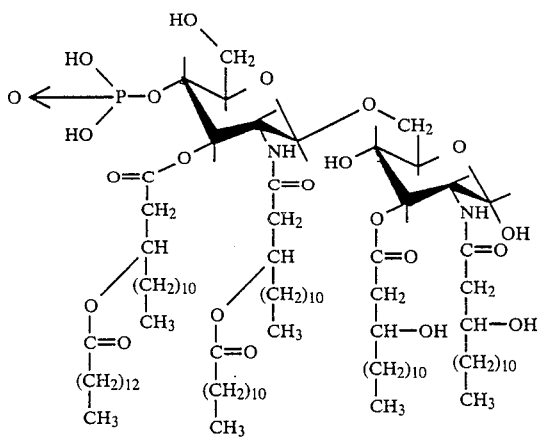

Monophosphoryl lipid A

MPL is a significant improvement over endotoxic extracts obtained from Enterobacteriaciae because MPL is detoxified and therefore does not contain the highly toxic components which have rendered endotoxic extracts unsuitable for therapeutic use. (See *Peptides as Requirements for Immunotherapy of the Guinea-Pig Line*-10 *Tumor with Endotoxins;* Tibi, et al. Cancer Immunol. Immunother. Vo. 7, pp 43–58: 1979, incorporated herein by reference. The beneficial effects of MPL over other endotoxic extracts is described for example in U.S. Pats. Nos. 4,436,727 and 4,436,728; and Ribi, E. Journal of Biological Response Modifiers, Vol 3, pp 1–9: 1984, incorporated herein by reference).

DETAILED DESCRIPTION OF THE INVENTION

Monophosphoryl lipid A (MPL), is prepared in the manner set forth in U.S. Pat. Nos. 4,436,727 and 4,436,728 incorporated herein by reference. More specifically, endotoxin extracts of the type used as the starting material to produce MPL may be obtained from any Enterobacteriaciae including parent organisms and mutants. The aforesaid patents described the type of microorganisms that may be used to obtain the starting material and several methods for preparing the starting material. The preferred method of obtaining the endotoxic extract is that disclosed by Chen et al., J. Infect. Dis 128 5433 (1973).

MPL as prepared above is combined with a pharmaceutically acceptable carrier such as, for example, a phosphate buffered saline solution, which can be injected parenterally (e.g. intravenously, introperitoneally, or intromuscularly). The composition contains from about 1 to 1000 micrograms of MPL, preferably about 25 to 200 micrograms, based on administration to a typical 70kg adult patient. The MPL containing composition when used to inhibit the onset of septicemia or endoxemia should be administered within about 24 hours and preferably within about 72 hours and again just before a patient is exposed to conditions under which septicemia or endotoxemia might arise.

As previously indicated, the Ziegler et al. reference discloses that anti-endotoxin serum can be used to treat patients suffering from gram-negative septicemia. In contrast, the present invention discloses the use of MPL to prevent septicemia. The treatment of Ziegler et al. does not disclose the use of endotoxin or its derivatives per se, but instead teaches the use of antibodies directed against endotoxin. This is evident from the two articles mentioned above. These articles discuss recent work of Ziegler and her colleagues, in which monoclonal antibodies (mAbs) against endotoxin are used instead of anti-endotoxin sera. Antiserum is a highly heterogeneous substance of ill-defined composition, whereas the mAbs used in these new references are pure substances of known structure. They are proteins, and they bear no resemblance whatsoever to endotoxin or MPL, which is emphasized in the present invention.

Further, it should be noted that Ziegler et al. teach that the anti-endotoxin serum or mAb is to be administered after the patient has become septicemic, i.e. it is to be used therapeutically (see p. 1226 of Ziegler et al., New Eng. J. Medicine, Vol 307, pp 1225–1230: 1982). In marked contrast to this, the present invention teaches that MPL is administered prior to the onset of septicemia, i.e. it is to be used prophylactically. The two approaches are therefore different. One is used to prevent septicemia, while the other is used to treat septicemia.

The present invention also differs in another important aspect. Thus, a further distinguishing feature is that the approach of Ziegler et al. is directed only towards treatment of gram-negative septicemia and associated endotoxemia, while the present invention can be used to prevent any kind of septicemia, whether caused by gram-negative or gram-positive organisms. The reason why the present invention does not suffer from the restrictions which apply to Ziegler et al. is again rooted in the differences between these two approaches. Ziegler et al. relies on an antibody which can bind to endotoxin and neutralize it. It is therefore only effective against organisms which produce endotoxin. In contrast to this, the present invention uses MPL to stimulate the immune system, so that infections can be quickly and efficiently eliminated. The MPL also produces a tolerance to endotoxin.

The present invention also differs from the procedures disclosed in the aforementioned references to Balogh et al. These references teach the use of radiation-detoxified endotoxin to treat septicemia. However, radiation-detoxified endotoxin is not a truly detoxified form of endotoxin since it will contains considerable endotoxin activity. Thus, Balogh et al. are essentially treating septicemia with a slightly less toxic endotoxin. Treatment of septicemia with low doses of endotoxin has been known since at least the early 1900's (see for example CA Johnson and SE Greisman. Mechanisms of Endotoxin Tolerance. In LB Hinsahw (ED), *Pathophysiology of Endotoxin*, Vol. 2, pp 359–401:1985 Elsevier, Amsterdam—N.Y.). It has never been reported in the literature, however, that a completely non-toxic form of endotoxin can be used to treat septicemia. The present invention therefore represents a marked improvement in the treatment of septicemia and endotoxemia.

A further important consideration is the chemical nature of radiation-detoxified endotoxin compared with that of MPL. Radiation-detoxified endotoxin is prepared by exposing aqueous solutions of endotoxin to gamma radiation from a $^{60}$Co source. The radiation causes a number of changes in the structure of the endotoxin. While the resulting complex product mixture has never been fractionated and characterized, it has been shown that most of the changes occur in the polysaccharide portion of the endotoxin molecule (see Csako et al., Radiation Research 105, 283:1986). The lipid A moeity, which is responsible for most of the biological activity of endotoxin, is relatively unaffected by the radiation. This results in a product that retains many of the biological activities of the starting endotoxin, including a relatively large degree of endotoxin toxicity.

In contrast to radiation-detoxified endotoxin, MPL has been purified to homogenicity and is fully characterized as shown by the aforementioned structural formula. It is a pure substance, and it exhibits virtually no endotoxin toxicity.

In order to demonstrate the residual toxicity in radiation-detoxified endotoxin in contrast to MPL, a comparison was made between a sample of this material as well as of the parent endotoxin from which it was made. A sensitive measure of endotoxin toxicity is the chick embryo 50% lethal dose assay ($CELD_{50}$). In this test, chick embryos at 10 days of age are injected with varying doses of the material to be tested. The number of surviving embryos at each concentration are tabulated 24 hours later, and this information can then be used to calculate an $LD_{50}$ (L. J. Reed and H. Muench. A simple method of estimating fifty percent points. Am. J. Hyg. 27 493:1939). The $CELD_{50}$ has been shown to correlate very well with other manifestations of endotoxicity, such as pyrogenicity (K. C. Milner and R. A. Finkelstein. Bioassay of endotoxin: Correlation between pyrogenicity for rabbits and lethality for chick embryos. J. Infect. Dis. 116, 529:1966). Using the chick embryo test, a comparison was made of the toxicity of radiation-detoxified endotoxin with the parent endotoxin as well as with MPL. The results are given below in Table A.

TABLE A

|  | Parent Endotoxin | Radio-Detoxified Endotoxin | Monophosphryl Lipid A |
|---|---|---|---|
| $CELD_{50}$ | 0.028 ug | 0.098 ug | >20 ug* |
| Phosphorous Content** | 2.5% | 2.9% | 1.8% |

*No eggs killed at any dose. For technical reasons, the highest dose is 20 ug/egg.
**Percent by weight These results demonstrate that radiation-detoxified endotoxin is only slightly less toxic than the starting endotoxin, whereas MPL showed essentially no toxicity in this assay. This indicates that the radiation-detoxified material still contains a considerable amount of residual endotoxic activity.

The relative phosphorous contents of endotoxin, radiation-detoxified endotoxin, and MPL are consistent with the $CELD_{50}$ values. As can be seen in the above table, radiation-detoxified endotoxin has a slightly higher phosphorous content than the parent endotoxin, while MPL has a considerably lower phosphorous content. MPL is made by chemically removing one of the phosphate groups present in lipid A, the toxic moiety of endotoxin. This treatment renders MPL completely non-toxic. If radiation-detoxified endotoxin were analogous to MPL, then one would expect it to have a much lower phosphorous content than it apparently has. The fact that radiation-detoxified endotoxin and the parent endotoxin have similar phosphorous contents is indicative that the toxic moiety, lipid A, is relatively unchanged by radiation treatment.

These differences between the MPL employed in the present invention and the endotoxins of the references are further elaborated in the following Table B, in which other toxic properties of radiation-detoxified endotoxin, endotoxin, and MPL are compared.

TABLE B

|  | Parent Endotoxin | Radiation-Detoxified Endotoxin | Monophosphoryl Lipid A |
|---|---|---|---|
| $LD_{50}$ in rats (mg/kg) | 20 (1) | 50 (1) | — |
| $LD_{50}$ in rabbits (mcg/kg) | .4–4 (2) | — | >8,000 (2) |
| Pyrogenicity in rabbits* | 2.4 (1) | 1.2 (1) | 0 (2) |
| Local Shwartzman+ Reaction in rabbits | 1,200 (1) | 600 (1) | <10 (3) |

*Difference between basic and maximal body temperature, expressed in °C.
+Area of hemorrhagic lesion, expressed in $mm^2$.
(1) L. Bertok. Radio-detoxified endotoxin as a potent stimulator of non-specific resistance. Perspect. Biol. Med. 24, 61 (1980).
(2) E. Ribi et al. Lipid A and Immunotherapy. Rev. Infect. Dis. 6, 567 (1984).
(3) K. Takayama et al. Influence of fine structure of lipid A on Limulus amebocyte lysate clotting and toxic activities. Infection and Immunity 45, 350 (1984).

The toxicity of radiation-detoxified endotoxin is only slightly attenuated relative to that of the parent endotoxin in all of these assays. MPL, on the other hand, shows only negligible toxicity in these assays. This is consistent with a complete lack of endotoxic activity in MPL, while radiation-detoxified endotoxin still shows considerable endotoxicity.

It has been known for years that low doses of endotoxin, i.e. less than the lethal dose, can be used to induce what is known as endotoxin tolerance. Such treatment will protect against both endotoxemia and septicemia. It is not surprising that radiation-detoxified endotoxin will also work in this way, since it is essentially just a moderately attenuated form of endotoxin. MPL, however, is completely lacking in the toxic attributes which characterize endotoxin. It is in a very real sense a different substance than endotoxin.

The following examples illustrate the best mode presently contemplated for the practice of this invention.

EXAMPLE 1

Protection Against the onset of Septicemia

14 NMRI mice were pretreated with one microgram of MPL administered by intraperitoneal injection. 24 hours later each of the mice underwent surgery wherein the cecum of each mouse was ligated and punctured to internally expose the mice to microorganisms capable of instigating the onset of septicemia. Upon completion of surgery, the animals were observed for 120 hours. A second group of mice were subjected to surgery in precisely the same way without pretreatment with MPL. The results are shown in Table C.

TABLE C

| NONSPECIFIC RESISTANCE TO SEPTICEMIA INDUCED IN MICE BY CECAL LIGATION AND PUNCTURE | | |
|---|---|---|
| Pretreatment | 120 hrs after induction of septicemia | |
| 1 μg, ip, 24 hr prior surgery | Dead/Total | % Survival |
| None | 11/14 | 21 |
| MPL (S. typhimurium) | 4/14 | 71 |

The foregoing results show that MPL inhibits the onset of septicemia.

EXAMPLE 2

Inhibition of non-septic endotoxemia.

A model for non-septic endotoxemia is to inject mice intraperitoneally (ip) with endotoxin. In this model, mice exposed to endotoxin exhibit ruffled fur, conjectival discharge, and diarrhea. Depending on the dose, death may occur within about 72 hours. The $LD_{50}$ can be determined by injecting groups of mice with different doses of endotoxin, and noting the number of survivors in each group. The protective effect of a given treatment is evidenced by an increase in the $LD_{50}$ of the endotoxin challenge.

In this embodiment, mice were injected ip on day 0 with either 100 ug MPL in 0.25 ml saline (treatment group) or else saline alone (control group). On day 3, mice in both groups received an ip injection containing one of several different doses of endotoxin (*E. coli* 0111:B 4). There were 8 mice at each endotoxin dose level. The doses for the control group were 0.50, 0.75, 1.00, 1.25, 1.50, and 1.0 mg endotoxin. The doses for treatment group were 0.75, 1.00, 1.25, 1.50, 2.0, and 2.5 mg endotoxin. The number of survivors in each group were noted for three days following the challenge. The $LD_{50}$ for each group was calculated using the method of Reed and Meuench (ibid.). The $LD_{50}$ for the control group was found to be 1.3 mg endotoxin. Since only 2 mice dies at the highest endotoxin dose in the treatment group, the $LD_{50}$ the $LD_{50}$ could not be calculated for this group. It is evident, however, that it would be well above 2.5 mg, probably around 5–6 mg. This would correspond to at least a 4 to 5 fold increase in the $LD_{50}$ following treatment with MPL.

In another experiment the $LD_{50}$'s for both the control and the treatment groups were successfully determined. The experimental design was essentially the same as that described above except that the endotoxin used was obtained from *E. coli* K235. The $LD_{50}$ for the control group in this experiment was 0.26 mg. The $LD_{50}$ for endotoxin in mice pre-treated with 100 ug MPL was 1.16 mg, corresponding to an increase of about a factor of 5. Furthermore, the MPL-treated animals did not show any of the usual symptoms of endotoxemia.

EXAMPLE 3

Inhibition of septic endotoxemia.

Injection of mice ip with live *E. coli* provides a good model of gram-negative sepsis and associated endotoxemia, since *E. coli* readily sheds endotoxin. In this model, a known quantity of live *E. coli* are injected, and the survivors are counted for an appropriate number of days. The effectiveness of a treatment is evidenced by an increase in the survivorship for a treated group.

In the experiment, 10 mice were given ip injections of 50 ug MPL on days 0 and 1. They therefore received a total of 100 ug MPL. The control group received only saline. All mice were challenged on day 2 with 5 $LD_{50}$'s of *E. coli* 055B5 organisms, also injected ip. All control animals died, whereas all treated animals (10/10) survived.

EXAMPLE 4

Inhibition of septic endotoxemia

In a manner similar to that employed in Example 3, 10 mice were given ip injections on days 0, 1 and 2 of 25, 25 and 50 ug MPL, respectively, corresponding to a total of 100 ug MPL for each mouse. Mice in the control group received only saline. On day 2, all mice received a challenge consisting of 30 $LD_{50}$'s of *E. coli* 055B5. This corresponds to an overwhelming challenge dose. No mice in the control group survived, while 50% animals (5/10) in the treatment group survived.

What is claimed is:

1. A method of inhibiting the onset of septicemia or septic and non-septic endotoxemia in a warm-blooded animal which comprises administering to said warm-blooded animal an effective amount of a composition comprising:
   (a) Monophosphoryl lipid A containing no detectable 2-keto-3-deoxyoctonoate, between about 350 and 475 nmoles/mg of phosphorus and between about 1700 and 2000 nmoles/mg of fatty acids; and
   (b) a pharmaceutically acceptable carrier.

2. A method of inhibiting the onset of septicemia in warm-blooded animals comprising administering to said warm-blooded animals an effective amount of a composition comprising:
   (a) Monophosphoryl lipid A containing no detectable 2-keto-3-deoxyoctonoate, between about 350 and 475 nmoles/mg of phosphorus and between about 1700 and 2000 nmoles/mg of fatty acids; and
   (b) a pharmaceutically acceptable carrier.

3. The method of claim 2, wherein said composition is in the form of a phosphate buffered saline solution.

4. The method of claim 2, wherein said composition is administered parenterally.

5. The method of claim 2, wherein said effective amount of the composition is between about 1 and 1000 mcg.

6. The method of claim 5, wherein said effective amount of the composition is between about 25 and 200 mcg.

7. The method of claim 5 wherein said effective amount of the composition is administered within about 72 hours prior to exposure to the conditions under which septicemia might arise.

8. A method of inhibiting the onset of septic and non-septic endotoxemia in warm-blooded animals comprising administering to said warm-blooded animals an effective amount of a composition comprising:
   (a) Monophosphoryl lipid A containing no detectable 2-keto-=3-deoxyoctonoate, between about 350 and 475 nmoles/mg of phosphorus and between about 1700 and 2000 nmoles/mg of fatty acids; and
   (b) a pharmaceutically acceptable carrier.

9. The composition of claim 8, in the form of a phosphate buffered saline solution.

10. The method of claim 8, wherein said composition is administered parenterally.

11. The method of claim 8, wherein said effective amount of the composition is between about 1 and 1000 mcg.

12. The method of claim 11, wherein said effective amount of the composition is between about 25 and 200 mcg.

13. The method of claim 11 wherein said effective amount of the composition is administered within about 72 hours prior to exposure to conditions under which endotoxemia might arise.

* * * * *